United States Patent
Oh et al.

(10) Patent No.: US 7,767,439 B2
(45) Date of Patent: Aug. 3, 2010

(54) REAL-TIME PCR MONITORING APPARATUS AND METHOD

(75) Inventors: Kwang-wook Oh, Gyeonggi-do (KR); Jin-tae Kim, Gyeonggi-do (KR); Kak Namkoong, Gyeonggi-do (KR); Chin-sung Park, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 832 days.

(21) Appl. No.: 10/890,350

(22) Filed: Jul. 13, 2004

(65) Prior Publication Data

US 2005/0130183 A1 Jun. 16, 2005

(30) Foreign Application Priority Data

Dec. 10, 2003 (KR) .................. 10-2003-0089352

(51) Int. Cl.
 C12M 1/34 (2006.01)
 C12M 3/00 (2006.01)
 C12Q 1/68 (2006.01)
 G01N 21/25 (2006.01)
(52) U.S. Cl. .................. 435/287.2; 435/6; 356/417
(58) Field of Classification Search .............. 435/287.5, 435/6, 287.52; 356/417
See application file for complete search history.

(56) References Cited

U.S. PATENT DOCUMENTS

| | | | | |
|---|---|---|---|---|
| 3,185,432 | A | * | 5/1965 | Hager, Jr. .................. 249/78 |
| 5,589,136 | A | * | 12/1996 | Northrup et al. ............. 422/102 |
| 6,264,825 | B1 | * | 7/2001 | Blackburn et al. ........ 205/777.5 |
| 6,369,893 | B1 | | 4/2002 | Christel et al. |
| 2002/0012910 | A1 | | 1/2002 | Weiss et al. .................... 435/6 |
| 2002/0072054 | A1 | * | 6/2002 | Miles et al. .................... 435/6 |

(Continued)

FOREIGN PATENT DOCUMENTS

KR 1020030073255 A 9/2003

OTHER PUBLICATIONS

Belgrader P, Benett W., Hadley D., Long G., Mariella R., Milanovich F., Nasarabadi S., Nelson W., Richards J., and Stratton P. Rapid pathogen detection using a microchip PCR array instrument. 1998. Clinical Chemistry 44:10 pp. 2191-2194.*

(Continued)

*Primary Examiner*—Walter D Griffin
*Assistant Examiner*—Lydia Edwards
(74) *Attorney, Agent, or Firm*—Cantor Colburn LLP

(57) ABSTRACT

A real time polymerase chain reaction ("PCR") monitoring apparatus includes, a microchip-type PCR tube that has a PCR solution-containing PCR chamber, a micro-heater, a detection unit detecting a PCR product signal based on the PCR solution, a plurality of modules, each of which includes the abovementioned elements in addition to a cooling fan and a control unit controlling the micro-heater and the cooling fan to adjust the temperature of the PCR chamber, a base instrument that comprises a power supply unit connected to the modules and a data communication unit connected to the control unit of each of the modules, and a display unit displaying data from the data communication unit, wherein the control unit of each of the modules independently controls at least one of both the detection unit and the temperature of the PCR chamber of the PCR tube in each of the modules.

8 Claims, 11 Drawing Sheets

U.S. PATENT DOCUMENTS

| | | | |
|---|---|---|---|
| 2002/0114734 A1 | 8/2002 | Pantoliano et al. | 422/67 |
| 2003/0169799 A1 | 9/2003 | Cho et al. | 374/31 |
| 2003/0190608 A1 | 10/2003 | Blackburn | 435/6 |
| 2004/0100284 A1* | 5/2004 | Lee et al. | 324/663 |
| 2004/0132059 A1* | 7/2004 | Scurati et al. | 435/6 |

OTHER PUBLICATIONS

Simultaneous Amplification and Detection of Specific DNA Sequences; Authors: Russell Higuchi, Gavin Dollinger, P. Sean Walsh and Robert Griffith; Bio/Technology vol. 10; Apr. 1992; pp. 413-417.

European Search Report for Application No. 04029339.1; Date of completion of search: Dec. 8, 2005.

Korean Office Action, Regarding Corresponding Patent Application No. 1020040102738, Date: Jun. 20, 2006. All references cited in the Office Action are listed above.

European Patent Office Examination Report; Issued Jun. 11, 2007.

\* cited by examiner

REAL-TIME PCR MONITORING APPARATUS AND METHOD

BACKGROUND OF THE INVENTION

This application claims priority from Korean Patent Application No. 2003-89352, filed on Dec. 10, 2003, in the Korean Intellectual Property Office, the disclosure of which is incorporated herein by reference in its entirety.

1. Field of the Invention

The present invention relates to a real-time polymerase chain reaction (hereinafter, simply referred to as PCR) monitoring apparatus and method. More particularly, the present invention relates to a real-time PCR monitoring apparatus with a combined PCR thermal cycler and PCR product detector, and a real-time PCR monitoring method using the apparatus.

2. Description of the Related Art

The science of genetic engineering originated with the discovery of restriction enzymes. Similarly, PCR technology led to an explosive development in the field of biotechnology, and thus, it may be said that the PCR technology is a contributor to the golden age of biotechnology. PCR is a technology to amplify DNA copies of specific DNA or RNA fragments in a reaction chamber. Due to a very simple principle and easy applications, the PCR technology has been extensively used in medicine, science, agriculture, veterinary medicine, food science, and environmental science, in addition to pure molecular biology, and its applications are now being extended to archeology and anthropology.

PCR is performed by repeated cycles of three steps: denaturation, annealing, and extension. In the denaturation step, a double-stranded DNA is separated into two single strands by heating at 90° C. or more. In the annealing step, two primers are each bound to the complementary opposite strands at an annealing temperature of 55 to 60° C. for 30 seconds to several minutes. In the extension step, primer extension occurs by DNA polymerase. The time required for the primer extension varies depending on the density of template DNA, the size of an amplification fragment, and an extension temperature. In the case of using Thermusaquaticus (Taq) polymerase, which is commonly used, the primer extension is performed at 72° C. for 30 seconds to several minutes.

Generally, PCR products are separated on a gel and the approximate amount of the PCR products is estimated. However, faster and more accurate quantification of PCR products is increasingly needed. Actually, an accurate measurement of the amount of target samples in gene expression (RNA) analysis, gene copy assay (quantification of human HER2 gene in breast cancer or HIV virus burden), genotyping (knockout mouse analysis), immuno-PCR, etc. is very important.

However, conventional PCR is end-point PCR for qualitative assay of amplified DNA by gel electrophoresis, which causes many problems such as inaccurate detection of the amount of DNA. To overcome the problems of the conventional end-point PCR, a quantitative competitive (QC) PCR method was developed. The QC-PCR is based on co-amplification in the same conditions of a target and a defined amount of a competitor having similar characteristics to the target. The starting amount of the target is calculated based on the ratio of a target product to a competitor product after the co-amplification. However, the QC-PCR is very complicated in that the most suitable competitor for each PCR must be designed, and multiple experiments at various concentrations for adjusting the optimal ratio range (at least a range of 1:10 to 10:1, 1:1 is an optimal ratio) of the target to the competitor must be carried out. The success probability for accurate quantification is also low.

In view of these problems of the conventional PCR methods, there has been introduced a real-time PCR method in which each PCR cycle is monitored to measure PCR products during the exponential phase of PCR. At the same time, there has been developed a fluorescence detection method for quickly measuring PCR products accumulated in a tube at each PCR cycle, instead of separation on a gel. UV light analysis of ethidium bromide-containing target molecules at each cycle and detection of fluorescence with a CCD camera were first reported by Higuchi et al. in 1992. Therefore, an amplification plot showing fluorescent intensities versus cycle numbers can be obtained.

However, in a conventional real-time PCR system, all wells or chips must be set to the same temperature conditions due to use of metal blocks such as peltier elements. Even though it may be advantageous to carry out repeated experiments using a large amount of samples at the same conditions, there are limitations on performing PCR using different samples at different temperature conditions. Also, since metal blocks such as peltier elements are used for temperature maintenance and variation, a temperature transition rate is low as 1 to 3° C./sec, and thus, a considerable time for temperature transition is required, which increases the duration of PCR to more than 2 hours. In addition, the temperature accuracy of ±0.5° C. limits fast and accurate temperature adjustment, which reduces the sensitivity and specificity of PCR.

SUMMARY OF THE INVENTION

The present invention provides a real-time PCR monitoring apparatus and method in which co-amplification of different samples at different temperature conditions can be carried out.

The present invention also provides a real-time PCR monitoring apparatus and method in which PCR can be performed for smaller amounts of unconcentrated samples at an enhanced temperature transition rate.

According to an aspect of the present invention, there is provided a real-time PCR monitoring apparatus comprising: a microchip-type PCR tube that has a PCR solution-containing PCR chamber; a micro-heater that applies heat to the PCR chamber of the PCR tube; a detection unit that detects a PCR product signal based on the amount of a PCR product of the PCR solution; a plurality of modules, each of which comprises a cooling fan for lowering the inside air temperature and a control unit for adjusting the temperature of the PCR chamber of the PCR tube by controlling the micro-heater and the cooling fan, and receives the PCR tube, the micro-heater, and the detection unit; a base instrument that comprises a power supply unit electrically connected to the modules for power supply and a data communication unit electrically connected to the modules for data communication with the control unit of each of the modules; and a display unit that displays data received from the data communication unit, wherein the control unit of each of the modules independently controls at least one of both the detection unit and the temperature of the PCR chamber of the PCR tube received in each of the modules.

The real-time PCR monitoring apparatus may further comprise an input unit that allows signal input to the control unit and the display unit.

The PCR product signal may be a fluorescence signal emitted from the PCR chamber and the detection unit may be a fluorescence detector that detects the fluorescence signal.

The PCR product signal may be an electrical signal measured in the PCR solution to which an alternating current is applied and the detection unit may comprise a sensor that detects the electrical signal.

The electrical signal may be a signal corresponding to impedance measured in the PCR solution.

The PCR tube may be made of silicon.

The micro-heater may be attached to a lower surface of the PCR tube.

According to another aspect of the present invention, there is provided a real-time PCR monitoring method comprising: (a) loading a PCR solution in a PCR chamber of a PCR tube received in each of a plurality of modules; (b) performing PCR independently in the PCR chamber of the PCR tube of each of the modules having an independently determined temperature condition; (c) detecting a PCR product signal based on the amount of a PCR product of the PCR solution in each of the modules; and (d) displaying data about the PCR product signal of each of the modules.

The PCR product signal may be a fluorescence signal emitted from the PCR chamber.

Step (c) may further comprise applying an alternating current to the PCR solution contained in the PCR chamber of the PCR tube of each of the modules, and the PCR product signal may be an electrical signal measured in the PCR solution.

The electrical signal may be a signal corresponding to impedance measured in the PCR solution.

The PCR tube may be made of silicon.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in detail with reference to the accompanying drawings.

Figure 1:
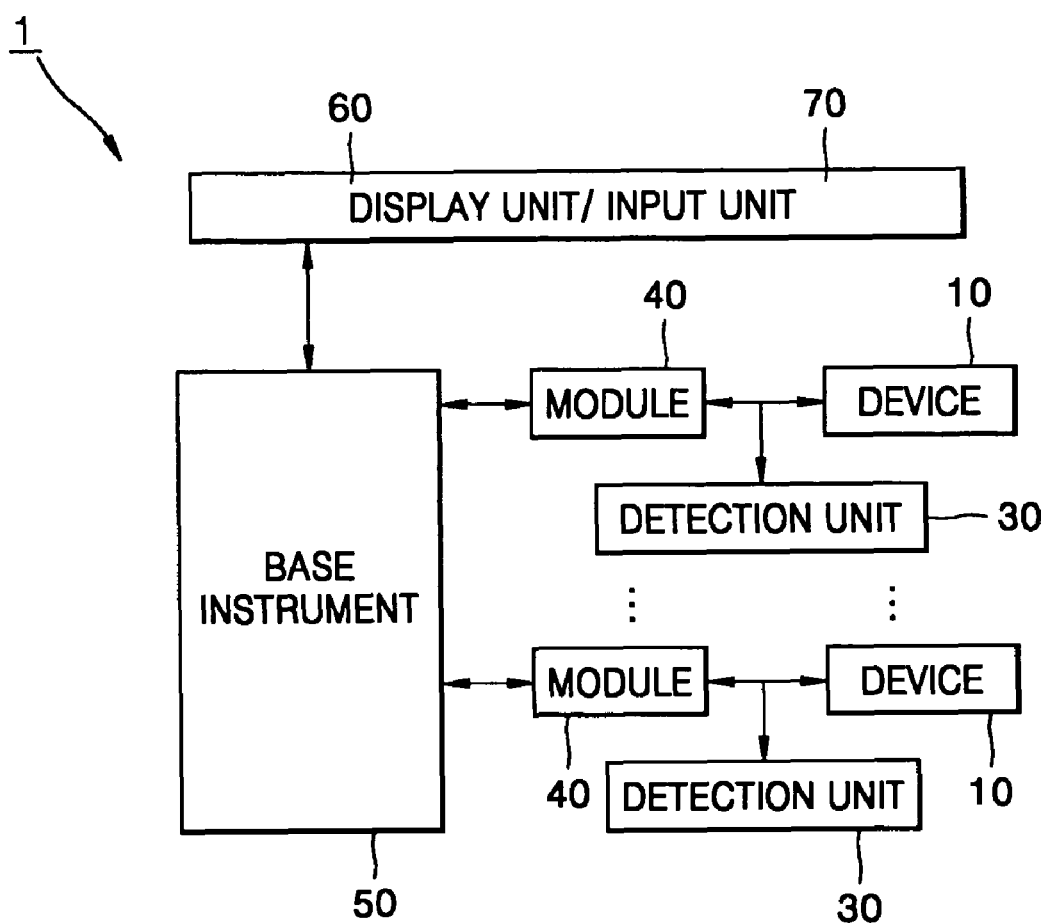
FIG. 1 is a schematic block diagram of a real-time PCR monitoring apparatus according to the present invention.

FIG. 1 is a schematic block diagram of a real-time PCR monitoring apparatus according to the present invention. Referring to FIG. 1, a real-time PCR monitoring apparatus 1 according to the present invention includes a device 10 having a PCR solution-containing PCR chamber 11 and a detection unit 30 for detecting a PCR product signal based on the amount of a PCR product of the PCR solution contained in the PCR chamber 11 of the device 10, a plurality of modules 40, each of which receives the device 10 and the detection unit 30, a base instrument 50 in which the modules 40 are detachably assembled, a display unit 60 for displaying data corresponding to a PCR product signal detected in the detection unit 30, and an input unit 70 that permits a user to input a signal. Here, the "device 10" may be used as the term that indicates a disposable and detachable device, generally a microchip-type PCR tube. However, the device 10 may be used as the term that covers a microchip-type PCR tube provided with a micro-heater and a sensor for sensing the temperature of the PCR tube, and a microchip-type PCR tube provided with a micro-heater, a sensor for sensing the temperature of the PCR tube, and another sensor for measuring the impedance of a PCR product. According to embodiments of the present invention, the display unit 60 and the input unit 70 are designed in the form of an integrated touch screen type monitor. Of course, the display unit 60 and the input unit 70 may also be respectively a monitor and a keyboard.

Figure 2:
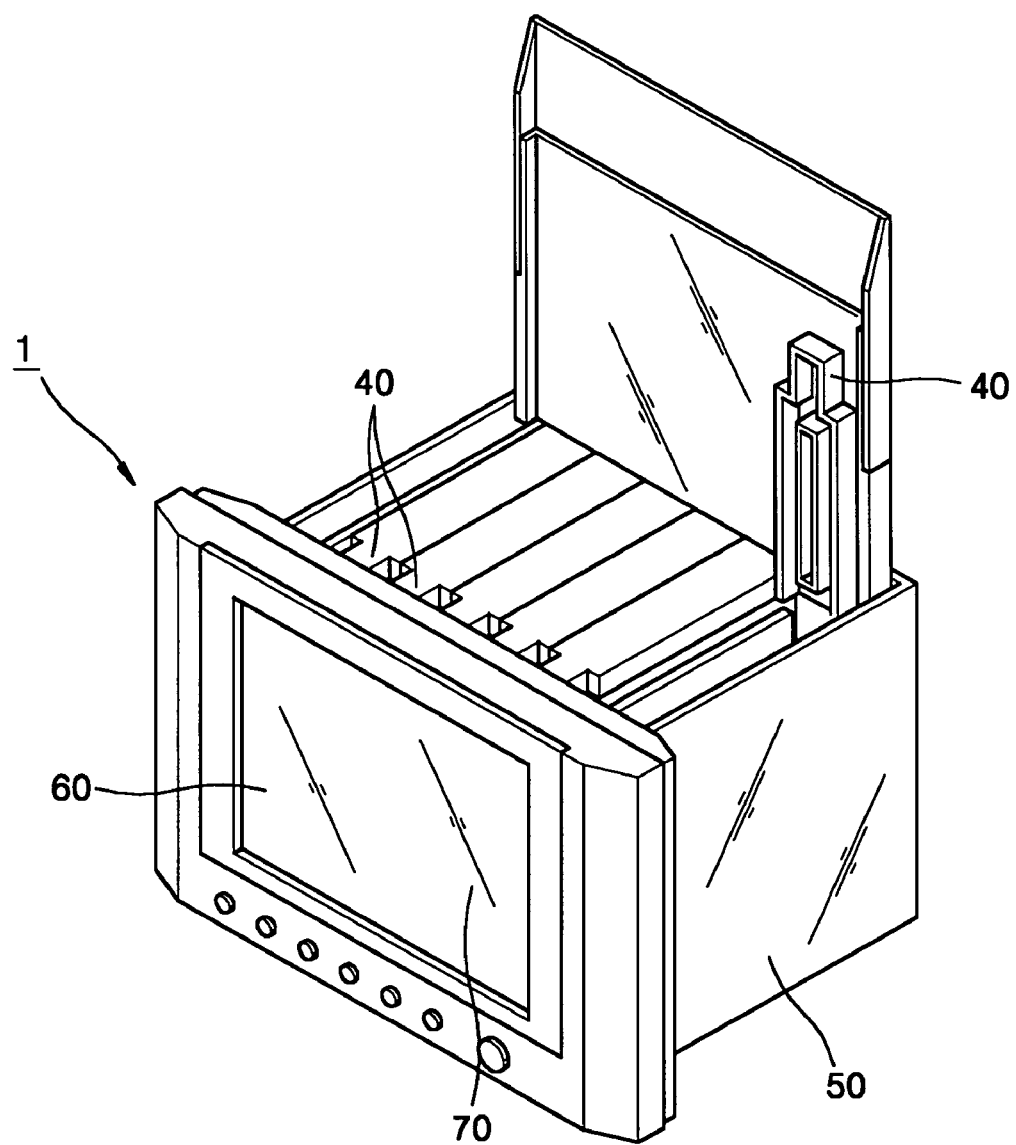
FIG. 2 is a schematic perspective view of a real-time PCR monitoring apparatus according to an embodiment of the present invention in which a PCR product signal is a fluorescence signal emitted from a PCR chamber.
Figure 3:
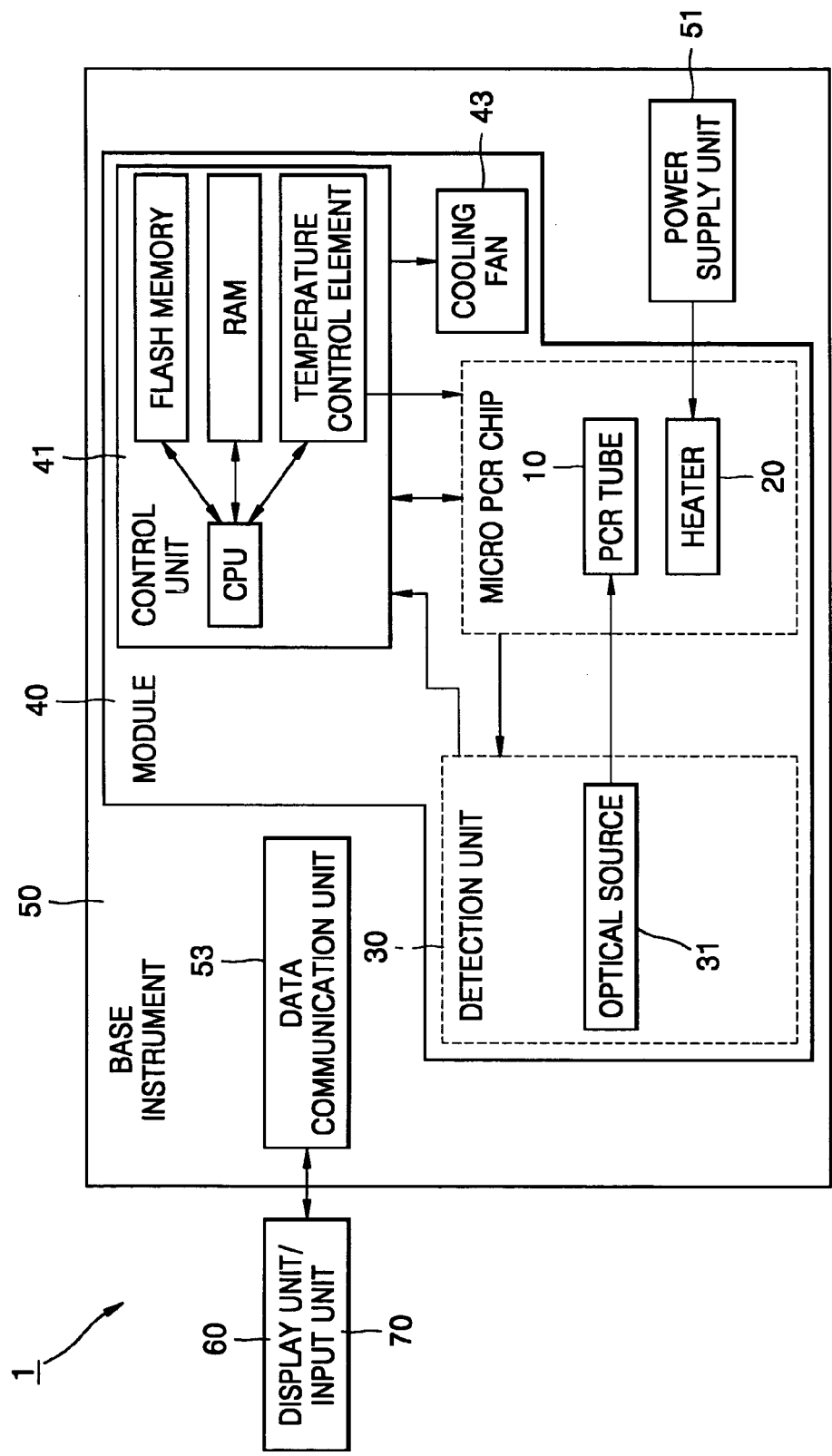
FIG. 3 is a block diagram that illustrates an operating principle of the real-time PCR monitoring apparatus of FIG. 2.

FIG. 2 is a schematic perspective view of a real-time PCR monitoring apparatus according to an embodiment of the present invention in which a PCR product signal is a fluorescence signal emitted from a PCR chamber and FIG. 3 is a block diagram that illustrates an operating principle of the real-time PCR monitoring apparatus of FIG. 2. Referring to FIGS. 2 and 3, a real-time PCR monitoring apparatus 1 according to an embodiment of the present invention includes a microchip-type PCR tube 10 having a PCR solution-containing PCR chamber 11, a micro-heater 20 for applying heat to the PCR chamber 11 of the PCR tube 10, and a detection unit 30 for detecting a PCR product signal based on the amount of the PCR product in the PCR solution, a plurality of modules 40, each of which receives the PCR tube 10, the micro-heater 20, and the detection unit 30, a base instrument 50 electrically connected to the modules 40, a display unit 60 for displaying data received from the base instrument 50, and an input unit 70 that permits a user to input a signal. As used herein, the modules 40 are composed of six numbers and are detachably assembled in the base instrument 50. The temperature of the PCR chamber 11 of the PCR tube 10 received in each of the modules 40 is independently adjusted by a control unit 41 of each of the modules 40 as will be described later.

Figure 4:
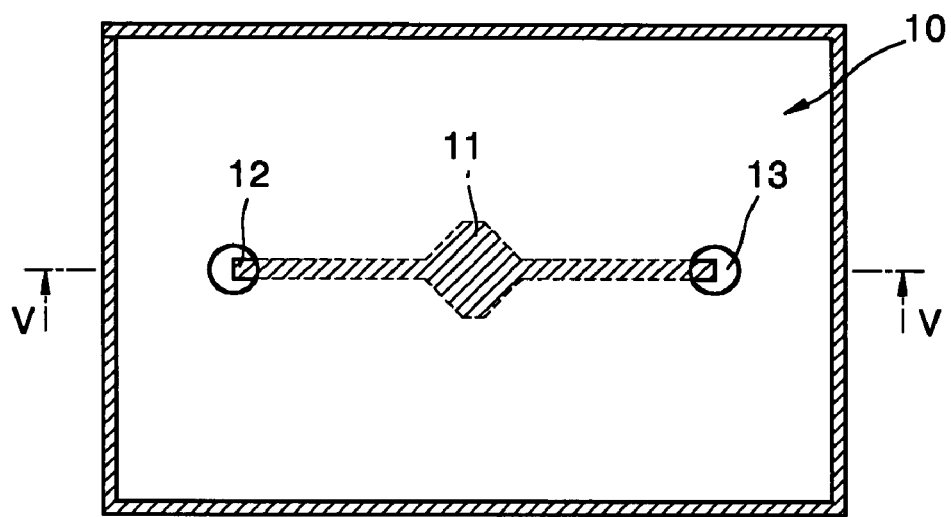
FIG. 4 is a plan view of a microchip-type PCR tube in the real-time PCR monitoring apparatus of FIG. 2.
Figure 5:
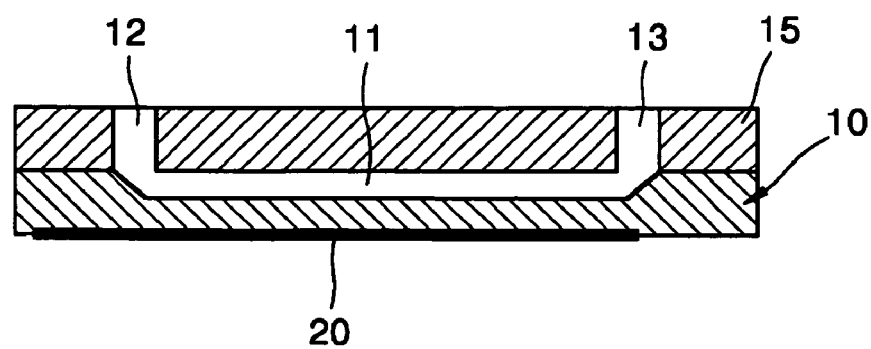
FIG. 5 is a sectional view taken along line V-V of FIG. 4.

FIG. 4 is a plan view of the microchip-type PCR tube 10 in the real-time PCR monitoring apparatus of FIG. 2, and FIG. 5 is a sectional view taken along line V-V of FIG. 4. Referring to FIGS. 4 and 5, the microchip-type PCR tube 10 is made of silicon and is formed with the PCR chamber 11 containing the PCR solution. The PCR chamber 11 has a sample inlet 12 for injection of the PCR solution and a sample outlet 13 for releasing of the PCR solution. A glass 15 is disposed on the PCR tube 10 made of silicon so that the detection unit 30 can detect a fluorescence signal emitted from the PCR product. The micro-heater 20 is attached to a lower surface of the PCR tube 10 to apply heat to the PCR tube 10.

According to the embodiment shown in FIGS. 2 and 3, the detection unit 30 is a fluorescence detector that detects a PCR product signal, i.e., a fluorescence signal emitted from the PCR chamber 11 and has an optical source 31 for applying light to the PCR solution. When light from the optical source 31 is applied to the PCR solution, the fluorescence emitted from the PCR solution is concentrated on a lens (not shown) of the fluorescence detector and recorded after passing through a filter.

Each of the modules 40 includes a cooling fan 43 for lowering the inside air temperature and the control unit 41 for adjusting the temperature of the PCR chamber 11 of the PCR tube 10 by controlling the micro-heater 20 and the cooling fan 43. The control unit 41 of each of the modules 40 independently adjusts the temperature of the PCR chamber 11 of the PCR tube 10 received in each of the modules 40.

A real-time PCR monitoring method using the real-time PCR monitoring apparatus 1 according to an embodiment of the present invention in which a PCR product signal is a fluorescence signal emitted from the PCR chamber 11 will now be described in detail with reference to FIG. 3. First, a touch screen type monitor that acts both as the display unit 60 and the input unit 70 receives PCR conditions, the power of an optical system, and signal measurement conditions, as input values. The input values are transmitted to the control unit 41 of each of the modules 40, specifically, a microprocessor. The control unit 41 permits the PCR tube 10 to have a predetermined temperature condition based on the temperature condition of the PCR tube 10 feedbacked from a signal processing circuit of the PCR tube 10. The control unit 41 also determines the operating and suspending time of the optical system of the detection unit 30 so that an optical signal can be measured in real time according to the measurement conditions. The control unit 41 also independently controls the temperature of the PCR tube 10 and the detection unit 30 in each of the modules 40, as described above.

Meanwhile, the base instrument 50 is electrically connected to each of the modules 40, and includes a power supply unit 51 for power supply to each of the modules 40 and a data communication unit 53 for data communication with the control unit 41 of each of the modules 40. In this embodiment, the modules 40 are composed of six numbers that are electrically connected to the base instrument 50.

Figure 6:
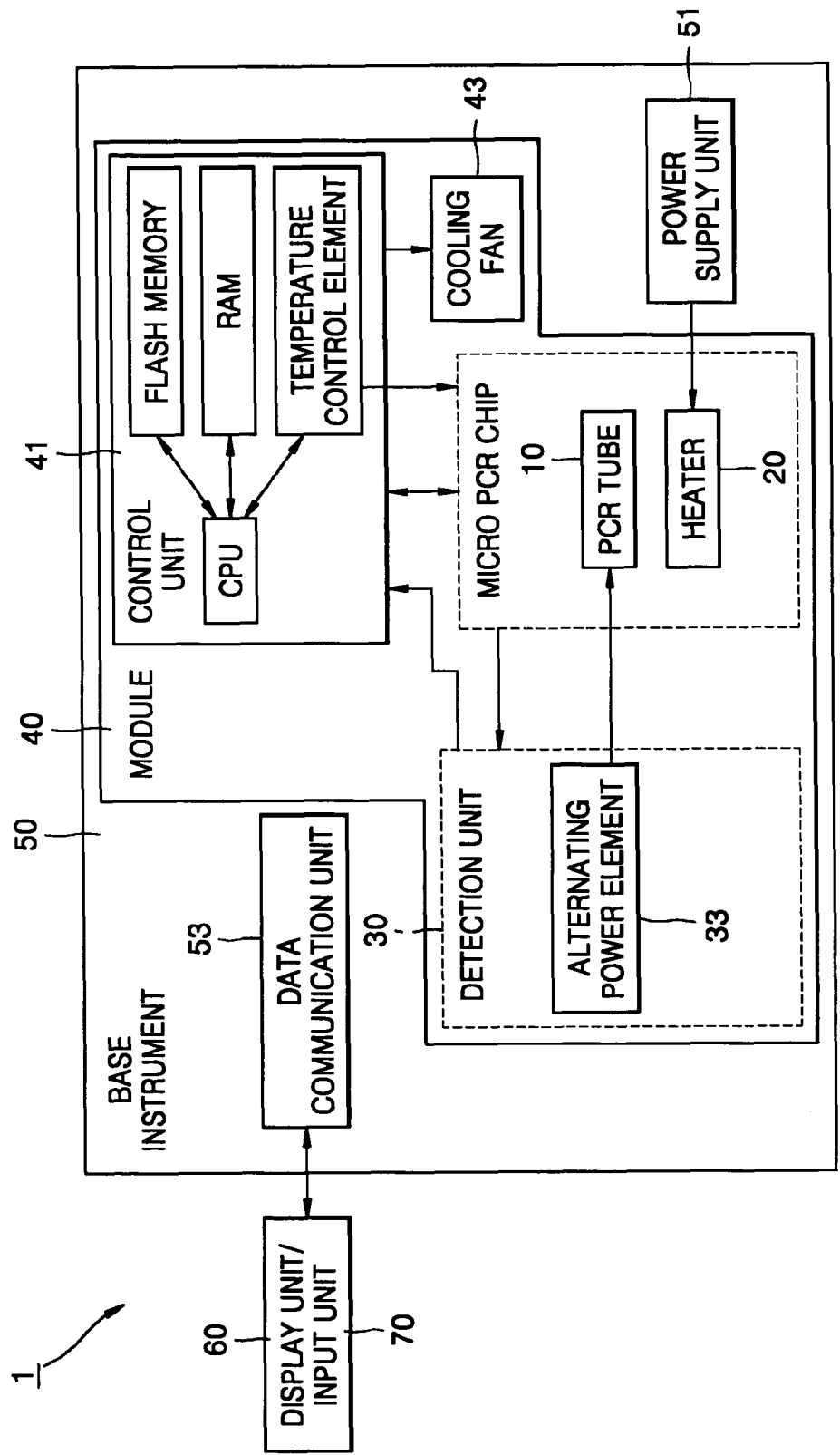
FIG. 6 is a block diagram that illustrates an operating principle of a real-time PCR monitoring apparatus according to another embodiment of the present invention in which a PCR product signal is a signal corresponding to impedance measured in a PCR product.

FIG. 6 is a block diagram that illustrates an operating principle of a real-time PCR monitoring apparatus according to another embodiment of the present invention in which a PCR product signal is a signal corresponding to impedance measured in a PCR product. This embodiment is different from the above-described embodiment only in that the detection unit 30 includes an alternating power element 33 and a sensor (not shown) for sensing an electrical signal, i.e., a signal corresponding to impedance measured in the PCR solution contained in the PCR chamber 11 during applying an alternating current to the PCR solution. Therefore, the same constitutional elements as in the above-described embodiment are designated the same reference numerals, and thus, overlapping descriptions are omitted.

A real-time PCR monitoring method according to the embodiment as shown in FIG. 6 will now be described. First, a touch screen type monitor that acts both as the display unit 60 and the input unit 70 receives PCR conditions, the magnitude and frequency of an alternating voltage for impedance measurement as input values. These input values are transmitted to the control unit 41 of each of the modules 40. The control unit 41 permits the PCR tube 10 to have a predetermined temperature based on the temperature condition of the PCR tube 10 feedbacked from a signal processing circuit of the PCR tube 10. The control unit 41 also determines the magnitude and frequency of an alternating voltage of the detection unit 30 so that impedance can be measured in real time according to the determined conditions. The control unit 41 of each of the modules 40 also independently controls the temperature of the PCR tube 10 and the detection unit 30 in each of the modules 40, as described above.

Figure 7:
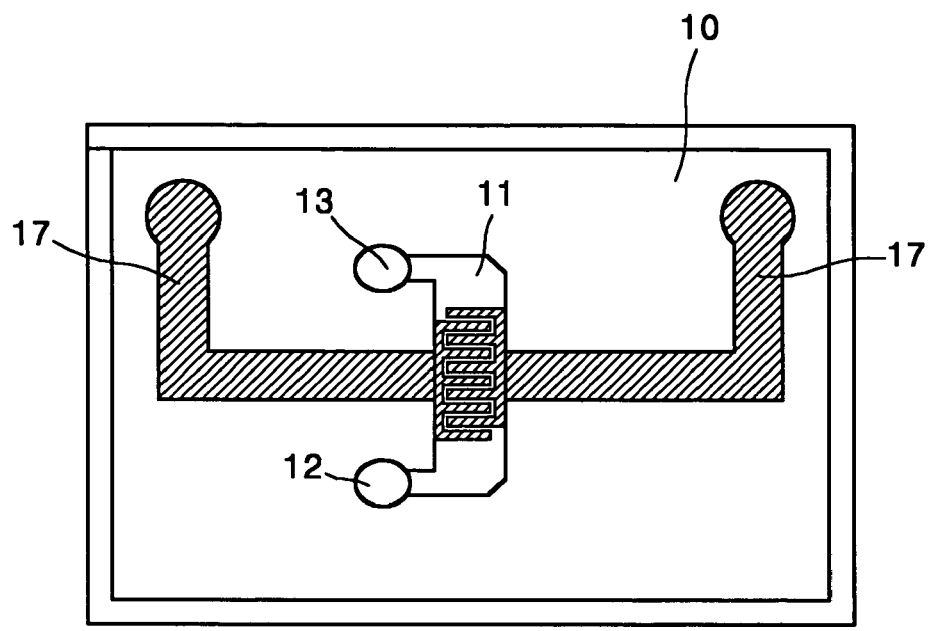
FIG. 7 is a plan view of a microchip-type PCR tube in the real-time PCR monitoring apparatus of FIG. 6.
Figure 8:
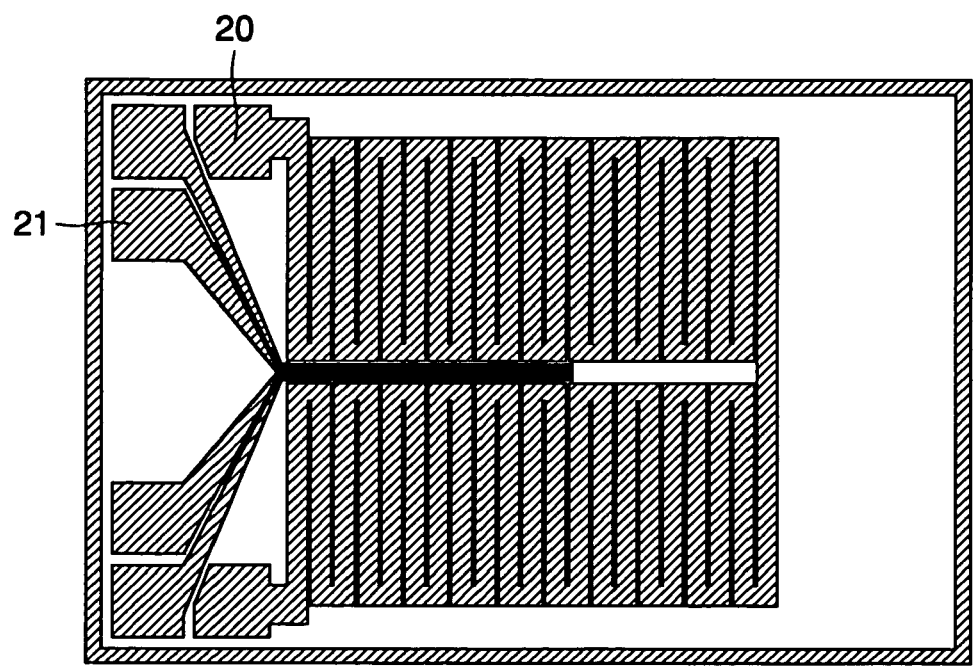
FIG. 8 is a rear view of the microchip-type PCR tube of FIG. 7.

FIG. 7 is a plan view of the microchip-type PCR tube 10 of the real-time PCR monitoring apparatus 1 of FIG. 6, and FIG. 8 is a rear view of the microchip-type PCR tube of FIG. 7. Referring to FIGS. 7 and 8, interdigitated electrodes 17 are disposed in the PCR chamber 11. Impedance measurement is performed while an alternating current is applied to a PCR mixture, i.e., the PCR solution. The micro-heater 20 made of a thin metal foil and a temperature sensor 21 enables temperature control on a chip.

Hereinafter, the present invention will be described more specifically by the following Examples. However, the following Examples are provided only for illustrations and thus the present invention is not limited to or by them.

EXAMPLE 1

Preparation of PCR Solution

To minimize difference between PCR experiments, other reagents except DNA samples were mixed to prepare a two-fold concentrated master mixture. Then, the master mixture was mixed with the DNA samples (1:1, by volume) to obtain a PCR solution.

The composition of the master mixture is as follows:

| | |
|---|---|
| PCR buffer | 1.0 μl |
| Distilled water | 1.04 μl |
| 10 mM dNTPs | 0.1 μl |
| 20 μM of each primer mixture | 0.2 μl |
| Enzyme mixture | 0.16 μl |

EXAMPLE 2

PCR on Microchips

To investigate the effect of a thermal transfer rate and a temperature ramping rate on PCR, PCR was carried out on micro PCR chips used in a real-time PCR monitoring apparatus of the present invention. The micro PCR chips used were made of silicon, and had advantages such as fast thermal transfer in reactants due to several hundreds times faster thermal conductivity than conventional PCR tubes, a fast temperature ramping rate, and maximal thermal transfer due to use of a trace of DNA samples.

1 µl of the PCR solution of Example 1 was loaded in each of the micro PCR chips, and a PCR cycle of 92° C. for 1 second and 63° C. for 15 seconds was then repeated for 40 times. The experimental resultants were quantified using Labchip (Agilent) and amplification was identified on a 2% TAE agarose gel.

Figure 9:
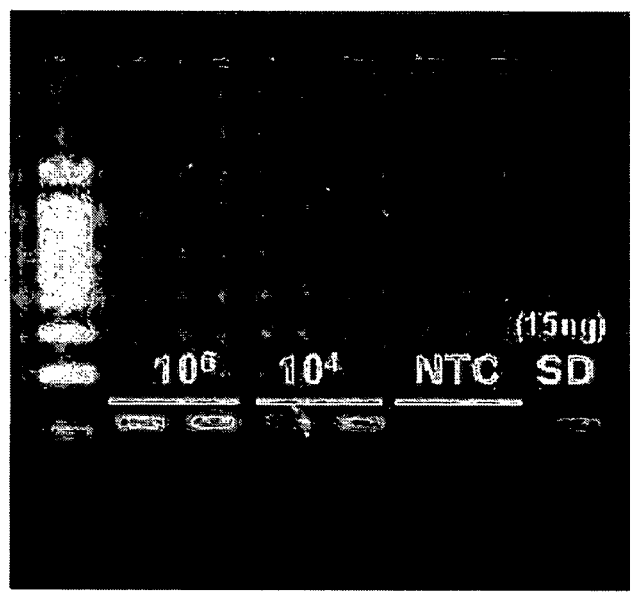
FIG. 9 illustrates an electrophoretic result on a 2% TAE agarose gel after two-stage PCR in a microchip-type PCR tube.

FIG. 9 shows electrophoretic results on a 2% TAE agarose gel after the amplification. Here, $10^6$ and $10^4$ indicate the copy numbers of a HBV template, NTC (no template control) is a negative control for PCR, and SD (standard) is a positive control for PCR.

Figure 10A:
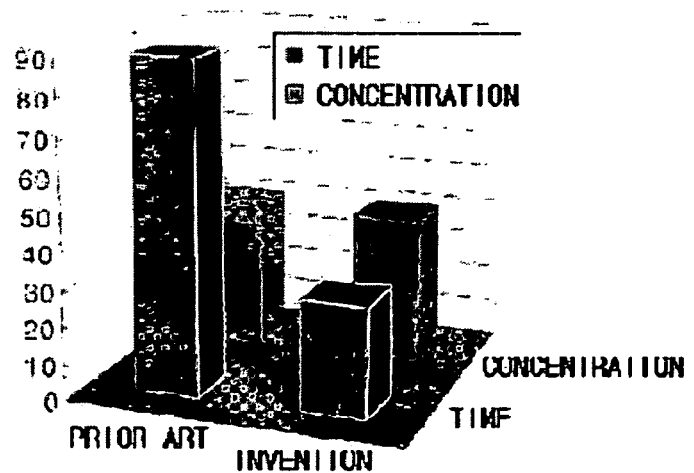
FIG. 10A is a comparative view that illustrates the duration of PCR required for obtaining almost the same DNA concentration in the present invention and a conventional technology.
Figure 10B:
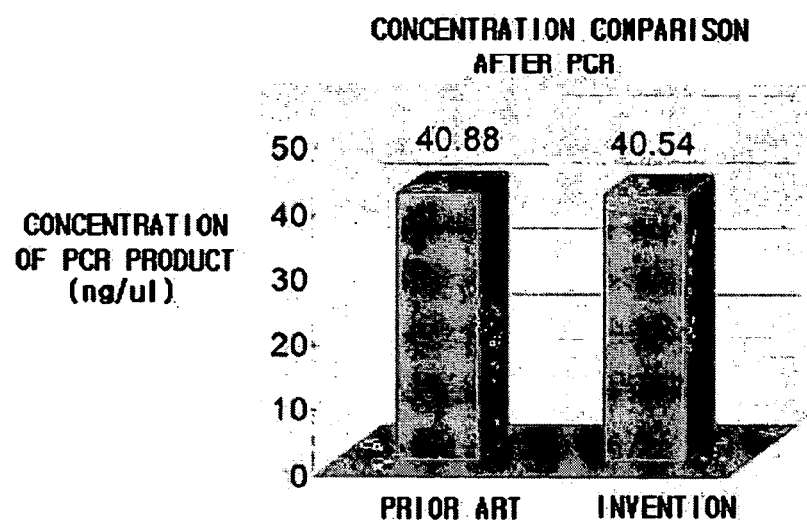
FIG. 10B is an enlarged view that illustrates only the DNA concentration of FIG. 10A.

FIGS. 10A and 10B are comparative views that illustrate the concentrations of PCR products with respect to the time required for PCR in a micro PCR chip according to the present invention and in a conventional PCR tube (MJ research, USA). Referring to FIGS. 10A and 10B, a time required for obtaining 40.54 ng/µl of a PCR product on a micro PCR chip according to the present invention was only 28 minutes. This is in contrast to 90 minutes required for obtaining 40.88 ng/µl of a PCR product using a conventional PCR tube. That is, a time required for obtaining the same concentration of a PCR product using the PCR technology of the present invention was only about one-third of that of using a conventional PCR tube.

Figure 11A:
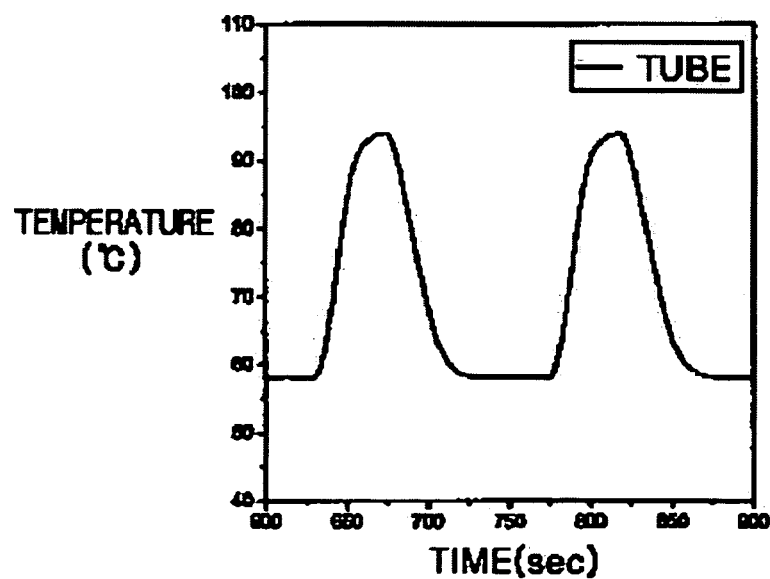
FIG. 11A is a graph that illustrates a temperature profile of a conventional PCR system.
Figure 11B:
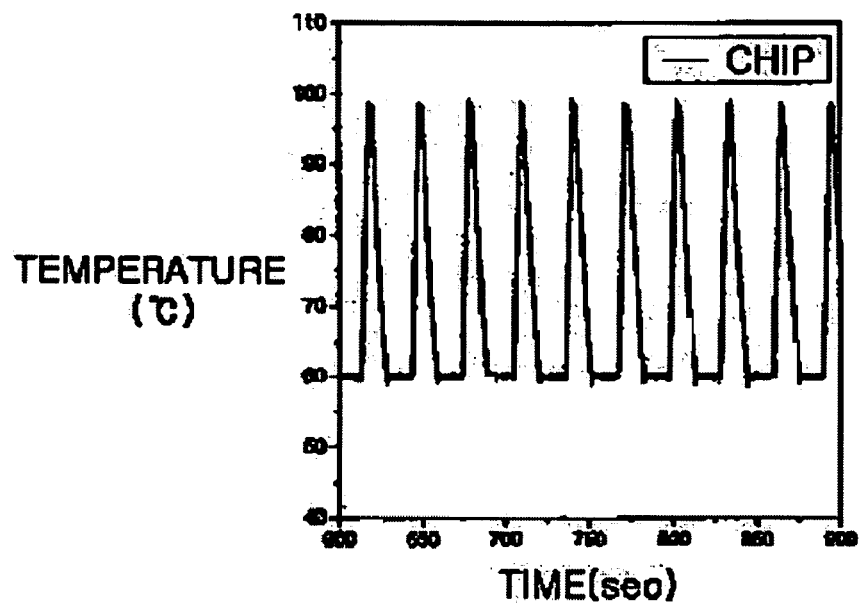
FIG. 11B is a graph that illustrates a temperature profile of a real-time PCR monitoring apparatus according to the present invention.

FIG. 11A is a graph that illustrates a temperature profile for a conventional PCR tube and FIG. 11B is a graph that illustrates a temperature profile for an apparatus according to the present invention.

EXAMPLE 3

Real-time PCR Monitoring Based on Signal Corresponding to Impedance Measured in PCR Product In this Example, a signal emitted from a PCR solution (Promega) was measured in real time using the apparatus of FIG. 6. To minimize difference between PCR experiments, the PCR solution was prepared as follows: other reagents except DNA samples were mixed to prepare a two-fold concentrated master mixture and then the master mixture was mixed with the DNA samples (1:1, by volume) to obtain the PCR solution.

The composition of the master mixture is presented in Table 1 below.

TABLE 1

| | Composition | Content |
|---|---|---|
| PCR buffer | Tris HCl | 10 mM |
| | KCl | 50 mM |
| | Triton X-100 | 0.10% |
| dNTP | dATP | 200 µM |
| | dCTP | 200 µM |
| | dGTP | 200 µM |
| | dUTP (dTTP) | 200 µM |
| Primer | Upstream | 1,000 nM |
| | Downstream | 1,000 nM |
| | Taq polymerase | 0.025 U/µl |
| | MgCl$_2$ | 1.5 mM |

The temperature and duration conditions for PCR were the same as those used in conventional PCR tubes as follows: 1 cycle of 50° C. for 120 seconds and 91° C. for 180 seconds; 1 cycle of 92° C. for 1 second and 63° C. for 180 seconds; 44 cycles of 92° C. for 1 second and 63° C. for 15 seconds; and 1 cycle of 63° C. for 180 seconds.

To measure impedance values, first, 1 µl of the PCR solution as prepared previously was loaded in each of micro PCR chips via a sample inlet as shown in FIGS. 7 and 8. After the micro PCR chips were received in modules, real-time impedance values were measured under an alternating voltage of 100 mV at 100 KHz.

Figure 12A:
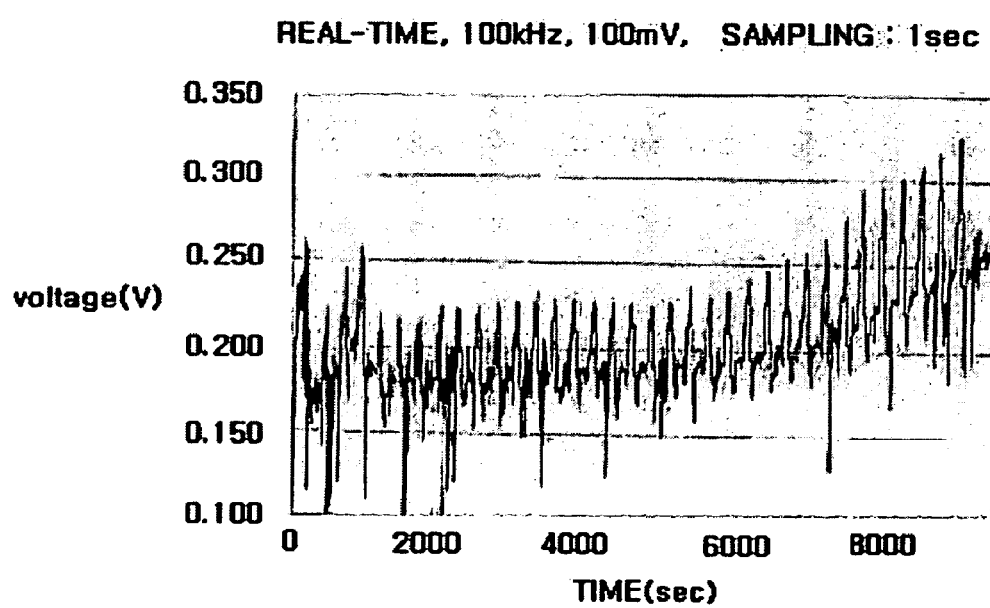
FIG. 12A is a view that illustrates real-time impedance values.
Figure 12B:
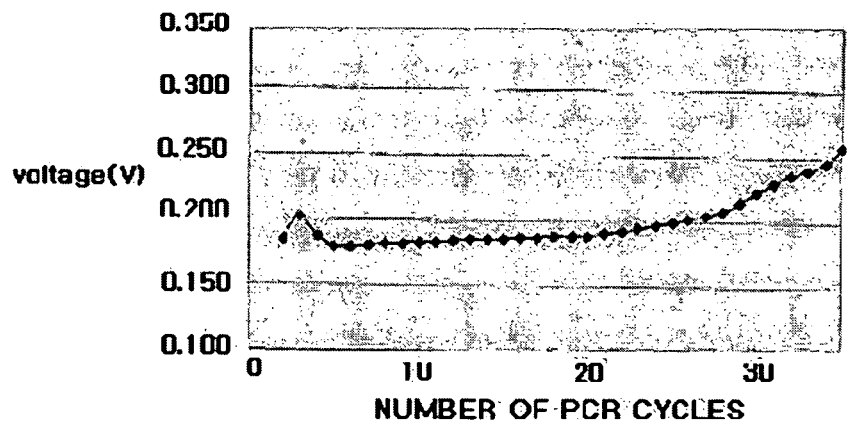
FIG. 12B is a graph that illustrates impedance values during extension versus the number of PCR cycles.

FIG. 12A shows the real-time impedance values and FIG. 12B is a graph that illustrates impedance values during extension versus the number of PCR cycles. As seen from FIGS. 12A and 12B, PCR products increased with time, and impedance increased from after about 28 cycles.

EXAMPLE 4

Real-Time Measurement and Visualization of Optical Signals

Two-stage thermal cycling for the PCR solution of Example 1 was performed according to the PCR conditions presented in Table 2 below.

TABLE 2

| Stage | Section | Temperature (° C.) | Duration (sec.) | Cycles |
|---|---|---|---|---|
| Stage 1 | Initial UNG incubation | 50 | 120 | 1 |
| | Initial denaturation | 89 | 60 | |
| Stage 2 | Denaturation | 89 | 10 | 40 |
| | Annealing | 65 | 30 | |
| | Detection time | Delay | 5 | |
| | | Measure | 23 | |
| Melting | Start temperature | 60° C. | | |
| | Stop temperature | 90° C. | | |
| | Ramping rate | 0.1° C./sec | | |
| | Heating rate | 10° C./sec | | |
| | Cooling rate | 5° C./sec | | |

Figure 13A:
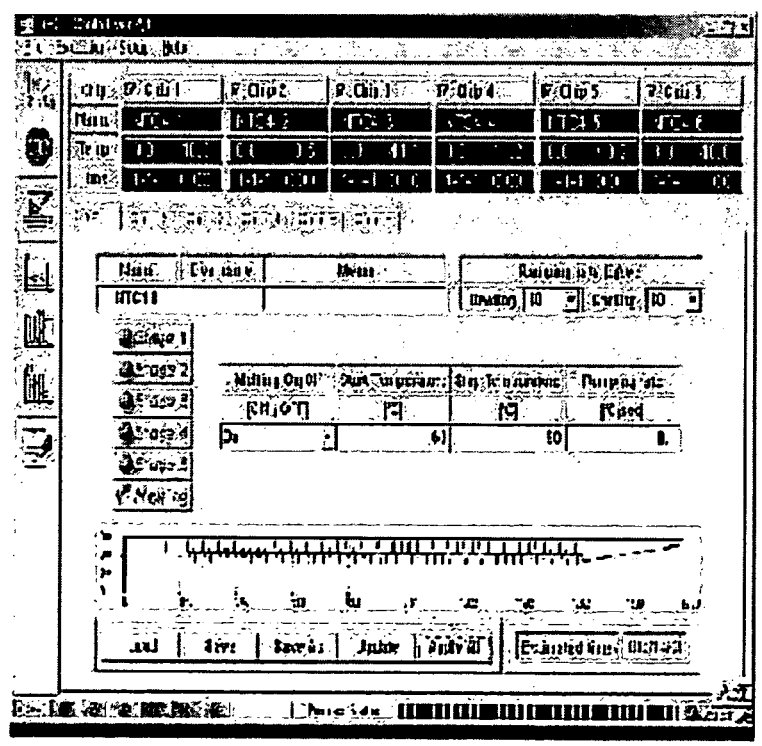
FIG. 13A is a view that illustrates real-time temperature profiles displayed on a screen of a real-time PCR monitoring apparatus according to the present invention.

First, 1 µl of the PCR solution of Example 1 was loaded in each of micro PCR chips via a sample inlet as shown in FIGS. 4 and 5. The micro PCR chips were received in modules and then thermal cycling for the micro PCR chips were performed according to the PCR conditions presented in Table 2 like in FIG. 13A.

Figure 13B:
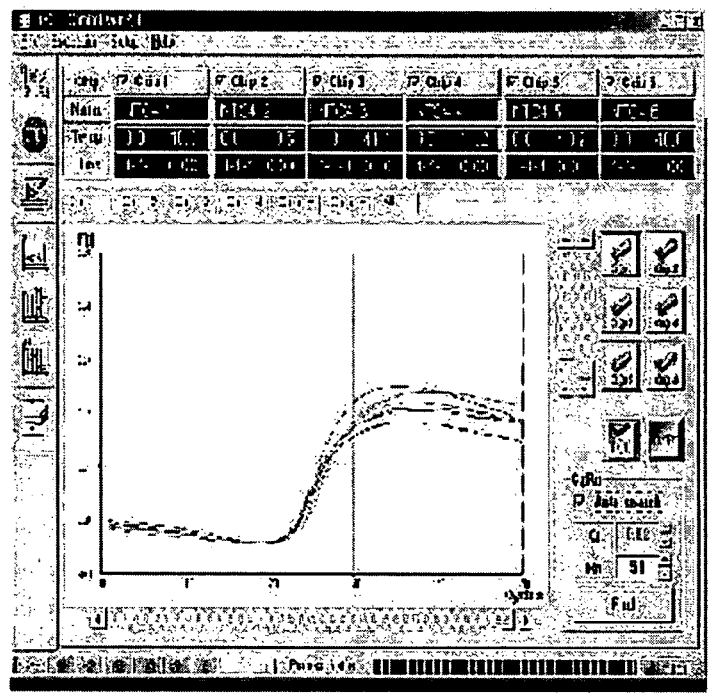
FIG. 13B is a view that illustrates real-time S-curves displayed on a screen of a real-time PCR monitoring apparatus according to the present invention.

FIG. 13B is a graph that illustrates real-time signal values measured for 23 seconds during annealing with respect to the number of PCR cycles. As seen from the graph, the amounts of PCR products exponentially increased with time and signal values increased from after about 25 cycles. That is, the graph with a S-shaped curve appears.

Figure 13C:
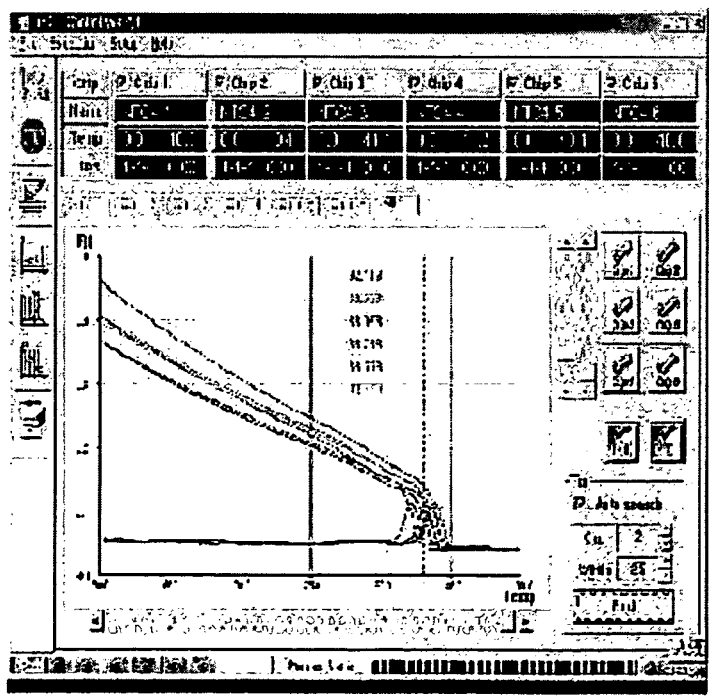
FIG. 13C is a view that illustrates real-time melting curves displayed on a screen of a real-time PCR monitoring apparatus according to the present invention.

FIG. 13C shows reduction of fluorescence signals due to separation of double-stranded DNAs into single-stranded DNAs with increasing temperature. Based on analysis of these fluorescence signal patterns, information about the melting temperatures of DNAs can be obtained. Creation of the melting curves of DNAs enables identification of desired DNAs after amplification.

As described above, a real-time PCR monitoring apparatus according to the present invention includes a microchip-type PCR tube having a PCR solution-containing PCR chamber, a micro-heater, a detection unit that detects a PCR product signal based on the amount of a PCR product in the PCR solution, a control unit that adjusts the temperature of the PCR chamber of the PCR tube, a plurality of modules, each of which receives the PCR tube, the micro-heater, and the detection unit, a base instrument electrically connected to the modules, and a display unit for data display. The control unit of each of the modules independently controls the detection unit and the temperature of the PCR chamber of the PCR tube received in each of the modules. Therefore, PCR for different samples can be carried out at different temperature conditions at the same time and can be monitored in real time.

In the above-described embodiments, a micro-heater is integrally attached to a lower surface of a microchip-type PCR tube. However, it is understood that a micro-heater may be installed in a module so that a microchip-type PCR tube can contact with the micro-heater after the PCR tube is received in the module provided with the micro-heater.

As apparent from the above descriptions, the present invention provides a real-time PCR monitoring apparatus and method in which co-amplification of different samples at different temperature conditions can be carried out.

The present invention also provides a real-time PCR monitoring apparatus and method in which PCR can be performed for smaller amounts of unconcentrated samples at an enhanced temperature transition rate using a microchip-type PCR tube made of silicon with excellent conductivity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A real-time PCR monitoring apparatus comprising: a microchip-type PCR tube that has a PCR solution-containing PCR chamber, wherein the PCR tube is made of silicon; a micro-heater that applies heat to the PCR chamber of the PCR tube, wherein the micro-heater comprises a metal foil layer disposed in a serpentine shape attached directly to a lower surface of the PCR tube; a detection unit that detects a PCR product signal based on the amount of a PCR product of the PCR solution, wherein the PCR product signal is an electrical signal measured in the PCR solution to which an alternating current is applied and the detection unit comprises a sensor that detects the electrical signal; a plurality of modules, each of which comprises a cooling fan for lowering the inside air temperature and a control unit for adjusting the temperature of the PCR chamber of the PCR tube by controlling the micro-heater and the cooling fan, and wherein each module of the plurality of modules receives the PCR tube, the micro-heater, and the detection unit; a base instrument that comprises a power supply unit electrically connected to the modules for power supply and a data communication unit electrically connected to the modules for data communication with the control unit of each of the modules; and a display unit that displays data received from the data communication unit, wherein the control unit of each of the modules independently controls at least one of the detection unit and the temperature of the PCR chamber of the PCR tube received in each of the modules, and wherein the micro-heater and PCR tube are detachably attached to the module as a single unit.

2. The real-time PCR monitoring apparatus of claim 1, further comprising an input unit that allows signals to be input to the control unit and the display unit.

3. The real-time PCR monitoring apparatus of claim 1, wherein the PCR product signal is a fluorescence signal emitted from the PCR chamber and the detection unit is a fluorescence detector that detects the fluorescence signal.

4. The real-time PCR monitoring apparatus of claim 1, wherein the electrical signal is a signal corresponding to impedance measured in the PCR solution.

5. A real-time PCR monitoring method comprising: (a) loading a PCR solution in a PCR chamber of a microchip-type PCR tube received in each of a plurality of modules, wherein the PCR tube is made of silicon; (b) performing PCR independently in the PCR chamber of the microchip-type PCR tube of each of the modules having an independently determined temperature condition, the independently determined temperature being controlled by a micro-heater comprising a metal foil layer disposed in a serpentine shape attached directly to a lower surface of the PCR tube; (c) detecting a PCR product signal based on the amount of a PCR product of the PCR solution in each of the modules, wherein the PCR product signal is an electrical signal measured in the PCR solution to which an alternating current is applied and the detection unit comprises a sensor that detects the electrical signal; and (d) displaying data about the PCR product signal of each of the modules.

6. The real-time PCR monitoring method of claim 5, wherein the PCR product signal is a fluorescence signal emitted from the PCR chamber.

7. The real-time PCR monitoring apparatus of claim 5, wherein the electrical signal is a signal corresponding to impedance measured in the PCR solution.

8. A real-time PCR monitoring apparatus comprising:
   a plurality of microchip-type PCR tubes that each have a PCR chamber, wherein each of the PCR tubes is made of silicon;
   a plurality of micro-heaters, each of which apply heat to the PCR chamber of at least one microchip-type PCR tube, wherein a single micro-heater of the plurality of micro-heaters comprises a metal foil layer disposed in a serpentine shape attached directly to a lower surface of a single PCR tube of the plurality of PCR tubes;
   a plurality of sensors, each of which detects an electrical signal from a PCR solution disposed in the PCR chamber of at least one of the plurality of microchip-type PCR tubes, wherein an alternating current is applied to the PCR solution;
   a plurality of modules, each of which comprises:
   a cooling fan; and
   a control unit,
   wherein each of the plurality of modules receives at least one of the plurality of microchip-type PCR tubes, at least one of the plurality of micro-heaters and at least one of the detection units, and the control unit of each module adjusts the temperature of the PCR chamber of the at least one of the plurality of microchip-type PCR tubes by controlling the at least one of the plurality of micro-heaters and the cooling fan;
   a base instrument which comprises:
   a power supply unit which supplies power to the plurality of modules; and
   a data communication unit in communication with the control unit of each of the plurality of modules; and
   a display unit which displays data received from the data communication unit,
   wherein the control unit of each of the modules independently controls at least one of the detection unit and the temperature of the PCR chamber of the PCR tube received in each of the modules, and
   wherein an individual micro-heater and an individual PCR tube are detachably attached to an individual module as a single unit.

* * * * *